United States Patent [19]
Nishioka et al.

[11] Patent Number: 5,091,795
[45] Date of Patent: Feb. 25, 1992

[54] OPTICAL LOW-PASS FILTER WITHOUT USING POLARIZERS

[75] Inventors: Kimihiko Nishioka, Hachiouji; Toshihito Kouchi, Tama; Takao Okada, Hachiouji, all of Japan

[73] Assignee: Olympus Optical Co., Ltd., Tokyo, Japan

[21] Appl. No.: 481,675

[22] Filed: Feb. 20, 1990

Related U.S. Application Data

[63] Continuation of Ser. No. 861,579, May 9, 1986, abandoned.

[30] Foreign Application Priority Data

May 11, 1985 [JP] Japan ............................ 60-100022

[51] Int. Cl.$^5$ ................................. G02F 1/13
[52] U.S. Cl. ............................ 359/93; 359/94; 359/53
[58] Field of Search ........... 350/347 R, 347 V, 347 E, 350/335, 337, 352, 96.1, 403, 404; 358/55

[56] References Cited

U.S. PATENT DOCUMENTS

| | | | |
|---|---|---|---|
| 2,718,170 | 9/1955 | Lyot | 350/404 |
| 3,040,625 | 6/1962 | Zito, Jr. | 350/336 |
| 3,588,224 | 6/1971 | Pritchard | 350/404 |
| 3,912,369 | 10/1975 | Kashnow | 350/347 R |
| 4,017,156 | 4/1977 | Moriyama et al. | 350/347 R |
| 4,136,053 | 1/1979 | Steinstrasser et al. | 350/350 R |
| 4,343,536 | 8/1982 | Watanabe et al. | 350/355 |
| 4,394,069 | 7/1983 | Kaye | 350/347 E |
| 4,416,514 | 11/1983 | Plummer | 350/335 |
| 4,562,831 | 1/1986 | Murakoshi et al. | 358/98 |
| 4,575,193 | 3/1986 | Greivenkamp, Jr. | 350/403 |
| 4,606,612 | 8/1986 | Iizuka | 350/347 R |
| 4,676,593 | 6/1987 | Adachi et al. | 350/96.1 |
| 4,678,287 | 7/1987 | Buhrer | 350/404 |

FOREIGN PATENT DOCUMENTS

| | | | |
|---|---|---|---|
| 0209716 | 12/1983 | Japan | 340/784 |
| 1390925 | 4/1975 | United Kingdom | 350/352 |

OTHER PUBLICATIONS

John W. Evans, "The Birefringent Filter", Journal of the Optical Society of America, vol. 39, No. 3.
Berezin et al., "Liquid Crystal Deflector", Sov. J. Quant. Electron, vol. 4, No. 5 (Nov. 1974).
Ludeman, "Liquid Crystal Cell having Nonuniform thickness", IBM Technical Disclosure Bulletin, vol. 15, No. 4, Sep. 1972.

Primary Examiner—Stanley D. Miller
Assistant Examiner—Trong Phan
Attorney, Agent, or Firm—Cushman, Darby & Cushman

[57] ABSTRACT

An optical low-pass filter comprising a liquid crystal device or electrooptic device having a birefringent phenomenon and formed so as to be able to vary the birefringent amount of the incident light. This low-pass filter is favorably used to remove the Moiré without so much reducing the resolving power in a television camera, electronic camera or fiberscope provided with a solid-state image sensor.

29 Claims, 9 Drawing Sheets

ORDINARY RAY COMPONENT  EXTRAORDINARY RAY COMPONENT

----- EXTRAORDINARY RAY COMPONENT
——— ORDINARY RAY COMPONENT

FIBERSCOPE SIDE  CCD SIDE

OPTICAL LOW-PASS FILTER WITHOUT USING POLARIZERS

This is a continuation of Application Ser. No. 06/861,579, filed May 9, 1986, which was abandoned upon the filing hereof.

BACKGROUND OF THE INVENTION a) Field of the Invention

This invention relates to an optical low-pass filter to be used to remove the Moiré in television cameras, electronic cameras and fiberscopes provided with a solid-state image sensor.

b) Description of the Prior Art

There is a problem that, in case an object having a geometrical pattern-shaped device is observed by using a solid-state image sensor such as CCD or an image guide or by using a combination of a solid-state image sensor and image guide, the Moiré, will be generated.

Therefore, in order to solve such problem, such optical low-pass filter made of such birefringent plate as a crystal plate as is shown in FIG. 1 has been placed between an imaging lens 2 and CCD3 as shown in FIG. 2 to cut high frequency component of the image of an object with birefringence to remove the Moiré.

However, there has been a problem that the optical low-pass filter made of a crystal plate or the like has a fixed crystal axis direction, therefore can not remove the Moiré as required, is low in the resolving power and is large in the thickness.

SUMMARY OF THE INVENTION

In view of the above mentioned problems, a primary object of the present invention is to provide an optical low-pass filter which can remove the Moiré as required, is not so low in the resolving power and can be made thin in the thickness.

The optical low-pass filter according to the present invention comprises a liquid crystal device or electrooptic device in which the direction of the crystal axis varies with the variation of the voltage to be applied to thereby enable to make a birefringent phenomenon as required and to displace most properly an image of an object to be observed in accordance with the object. Further, the present invention utilizes the fact that such device has a birefringent index much higher than of a crystal plate or the like.

Another object of the present invention is to provide an optical low-pass filter which can be favorably used for television cameras, electronic cameras and fiberscopes provided with solid-state image sensors.

These and other objects as well as the features and advantages of the present invention will be apparent from the following detailed description of the preferred embodiments when taken in conjunction with the accompanying drawings.

DESCRIPTION OF THE PREFERRED EMBODIMENT

Figure 1:
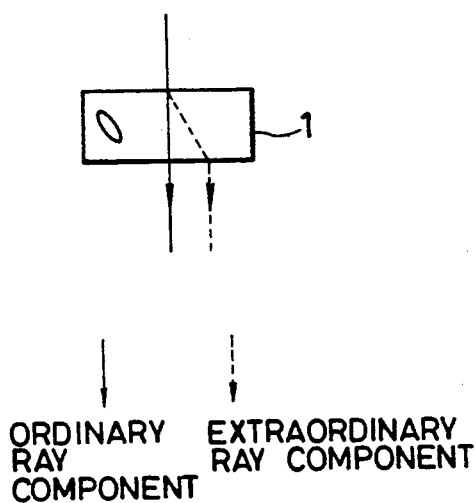
FIG. 1 is a schematic sectional view of a conventional optical low-pass filter.
Figure 2:
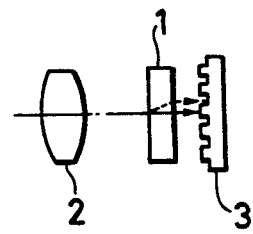
FIG. 2 is a view showing the optical low-pass filter of FIG. 1 as being used.
Figure 3:
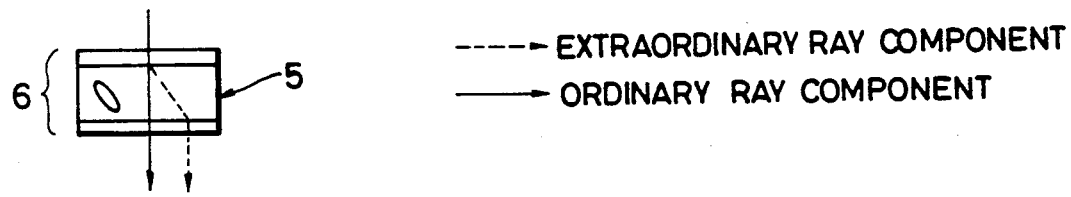
FIG. 3 is a schematic sectional view of the first embodiment of a low-pass filter according to the present invention.

The present invention shall be explained in detail in the following on the basis of the illustrated respective embodiments:

FIG. 3 shows the first embodiment in which an optical low-pass filter 6 consists of a liquid crystal device 5 wherein the orientation of the liquid crystal (direction of the crystal axis) is inclined with respect to the optical axis. The value of $n_e$ (the refractive index for the extraordinary ray component)—$n_o$ (the refractive index for the ordinary ray component) is so large as to be, for example, 0.255 in MBBA (N—p—methoxybenzylidene—p'—n—butylaniline) which is much larger than $n_e-n_o=0.0091$ in the crystal plate. Therefore, an optical low-pass filter thin in the thickness can be made. If it is arranged the same as in the above mentioned conventional example, the Moiré will be able to be removed.

Figure 4A:
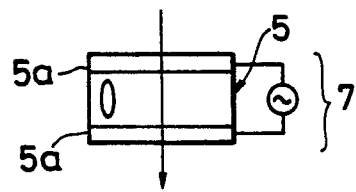
FIGS. 4A, 4B and 5A, 5B are schematic sectional views respectively of the second and third embodiments.
Figure 4B:
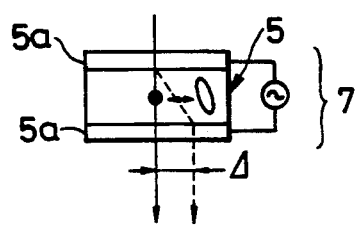

FIGS. 4A and 4B show the second embodiment in which an optical low-pass filter 7 is made to continuously vary the displacement Δ of the image by the birefringence by varying the orientation of the liquid crystal device 5 by varying the voltage applied to transparent electrodes 5a, 5a. Therefore, if it is used, the birefringent phenomenon will be able to be generated as required and therefore, as required, the Moiré will be able to be removed. Also, if the displacement Δ of the image is made to be of a proper size, as detailed later, the Moiré will be able to be removed without so much reducing the resolving power. By the way, Δ may be constant or varied during the observation of the image.

Figure 5A:
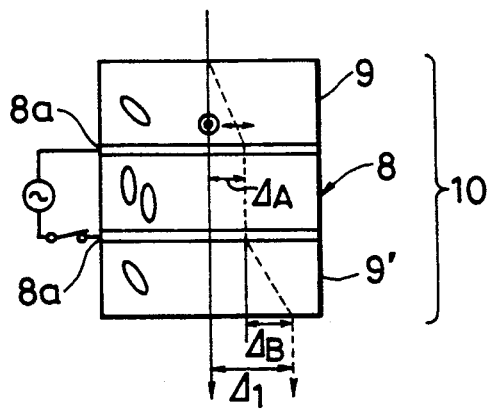
Figure 5B:
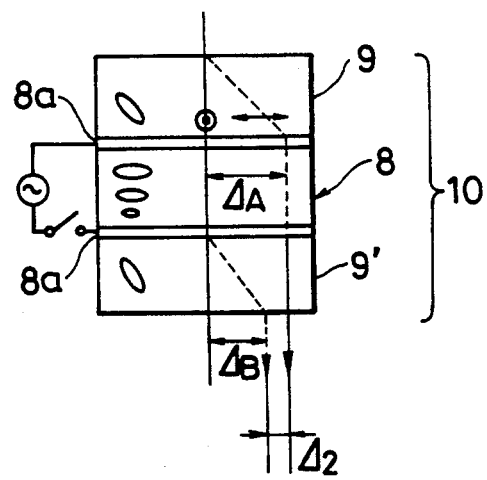

FIGS. 5A and 5B show the third embodiment in which an optical low-pass filter 10 is made by arranging crystal plates 9, 9' of the same inclination direction of the crystal axis in front and rear of a twisted nematic type liquid crystal device 8. The birefringent amount is made $\Delta_1$ and $\Delta_2$ by varying the optical rotatory power of the liquid crystal device 8 by switching on-off the voltage applied to transparent electrodes 8a, 8a. There is an advantage that the liquid crystal device 8 is so thin as to be 7 to 8 microns in the thickness and therefore the transmittance is high. By the way, in this case, there will be established $$\left.\begin{array}{l}\Delta_1 = \Delta_A + \Delta_B \\ \Delta_2 = \Delta_A - \Delta_B\end{array}\right\} \quad (1)$$

where $\Delta_A$ and $\Delta_B$ are birefringent amounts by the crystal plates 9 and 9' and $\Delta_A > \Delta_B$.

Figure 6:
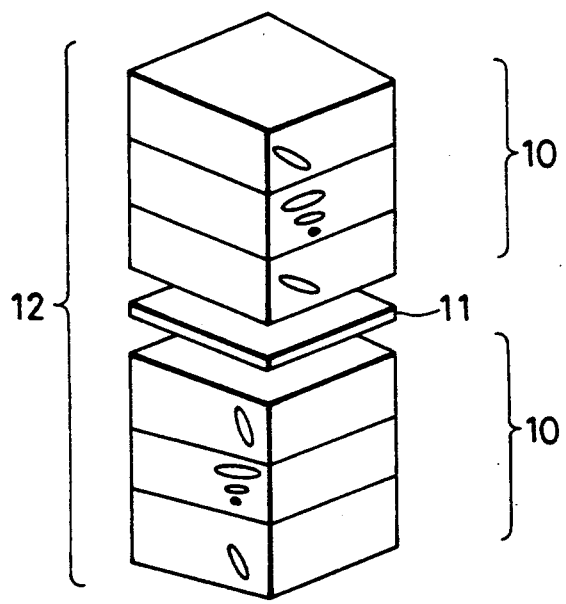
FIG. 6 is a perspective view of the fourth embodiment.
Figure 8:
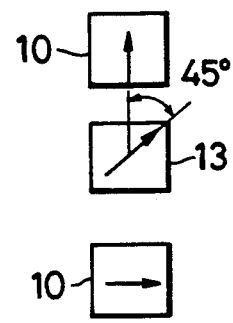
FIG. 8 is a view showing the direction of the crystal axis of a crystal plate to be used in the fourth embodiment.
Figure 7A:
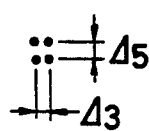
FIGS. 7A to 7D are views showing displacement of an image by the fourth embodiment.
Figure 7B:
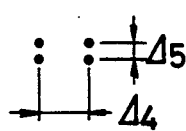
Figure 7C:
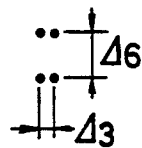
Figure 7D:
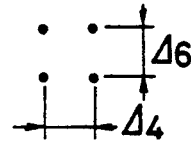

FIG. 6 shows the fourth embodiment in which two low-pass filters 10 of the above mentioned third embodiment are overlapped on each other so that the planes including the respective crystal axes may intersect rectangularly or obliquely with each other and a ¼-wave plate 11 (having a function of making a linearly polarized light a circularly polarized light) is arranged between the two low-pass filters 10. By varying the voltages applied respectively to the low-pass filters 10, 10 and, by the birefringence, as shown in FIGS. 7A to 7D, the rays of light can be divided substantially in one place (FIG. 7A), substantially in two places (FIG. 7B or 7C) or in four places (FIG. 7D) where $\Delta_3$ and $\Delta_4$ represent displacements of the image by one low pass filter 10 and $\Delta_5$ and $\Delta_6$ represent displacement of the image by the other low-pass filter 10. By the way, instead of the ¼-wave plate 11, there may be used a polarization canceling plate, an optical rotatory plate of ±45 degrees or such birefringent plate 13 as a crystal plate having a crystal axis inclined by 45 degrees as shown in FIG. 8. The arrow of the birefringent plate 13 in FIG. 8 shows the direction of the crystal axis of the birefringent plate 13 as seen in the incident direction of the light. The arrow of the low pass filter 10 in FIG. 8 shows the separating direction of the light of the low-pass filter 10 as seen in the incident direction of the light.

Figure 9A:
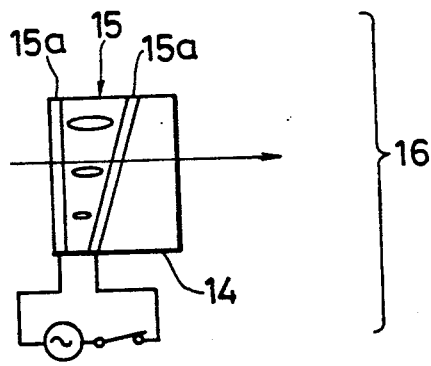
FIGS. 9A and 9B are schematic sectional views of the fifth embodiment.
Figure 9B:
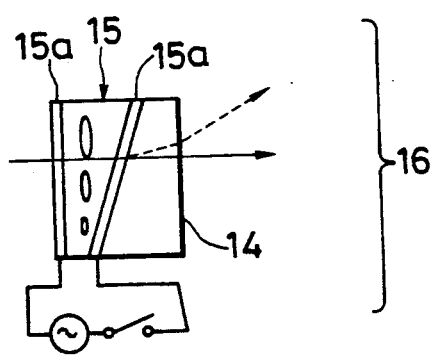
Figure 10:
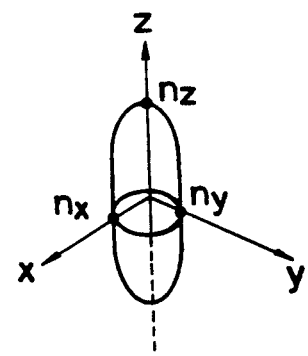
FIG. 10 is a view showing an index ellipsoid of the liquid crystal of the fifth embodiment.
Figure 11:
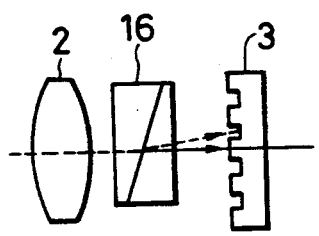
FIG. 11 is a view showing the fifth embodiment as being used.

FIGS. 9A and 9B shows the fifth embodiment in which an optical low-pass filter 16 consists of an N-type liquid crystal device 15 having a prism 14 on the rear side and having transparent electrodes 15a on the prism 14 side as inclined to the optical axis. There is utilized the birefringence, that is, the fact that the natural light incident upon the liquid crystal device 15 is different in the refractive index by the liquid crystal depending on an ordinary ray component or extraordinary ray component, is therefore different in the refractive index on the boundary surface with the prism 14 and will advance as separated in two directions having angles when it is projected. In such case, by switching on-off the voltage applied to the transparent electrodes 15a, 15a, the birefringent phenomenon can be produced or canceled. By the way, the liquid crystal within the N-type liquid crystal device 15 may have such refractive index ellipsoid as is shown in FIG. 10 and the refractive index of the prism 14 may be substantially equal to $n_x$ or $n_y$. Also, in order to remove the Moiré, the low-pass filter 16 may be arranged between the imaging lens 2 and CCD3 as shown in FIG. 11.

Figure 12A:
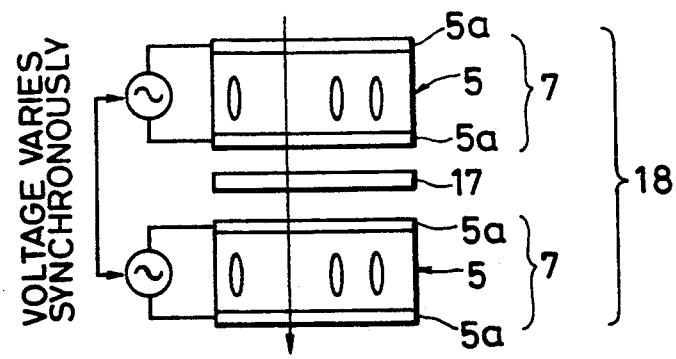
FIGS. 12A, 12B and 13A, 13B are schematic sectional views respectively of the sixth and seventh embodiments.
Figure 12B:
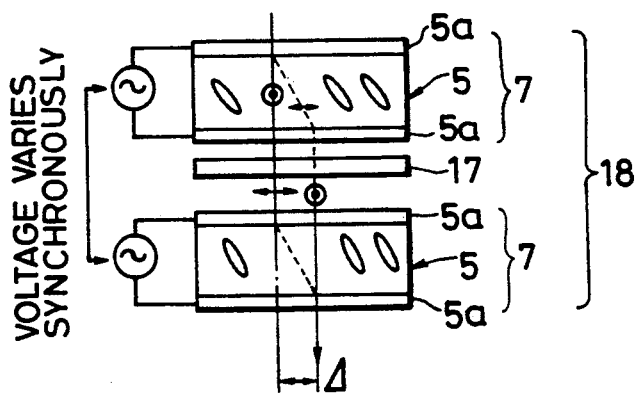

FIGS. 12A and 12B show the sixth embodiment in which an optical low-pass filter 18 consists of two low-pass filters 7 of the above mentioned second embodiment (See FIGS. 4A and 4B) overlapped on each other and a ½-wave plate 17 arranged between them to remove the Moiré by shaking and obscuring the image before the CCD3. For that purpose, when a driving voltage is synchonously applied to two liquid crystal devices 7 and 7, the incident light to the optical low-pass filter 18 will be first separated the ordinary ray component and the extraordinary ray component by the first liquid crystal device 7. As each polarization plane of the ray components is rotated by 90 degrees by the ½-wave plate, the above mentioned ordinary ray component and extraordinary ray component will be exchanged to each other to the second liquid crystal device 7. Therefore, the ordinary ray component to the first liquid crystal device will be refracted by the second liquid crystal device and will issue therefrom along with the extraordinary ray component at the position displaced by Δ from the incident position onto the second liquid crystal device. The exit position of the exit light will result in oscillation with an amplitude Δ by changing the amplitude of the driving voltage at a speed higher than a predetermined value (for example, at a speed higher than twice the read-out period of the CCD). The displacement Δ will vary continuously and periodically or at random when the wave shape of the voltage to be applied is varied. By the way, instead of the ½-wave plate 17, there may be used an optical rotatory plate rotating the plane of polarization by 90 degrees or a twisted nematic type liquid crystal.

Figure 13A:
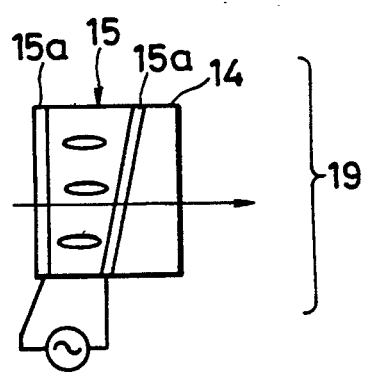
Figure 13B:
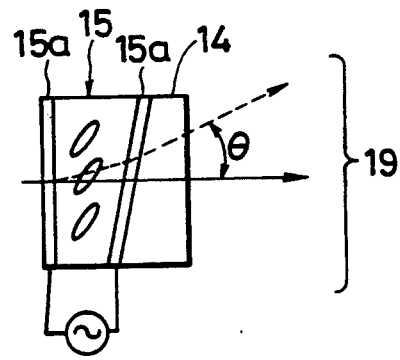
Figure 14:
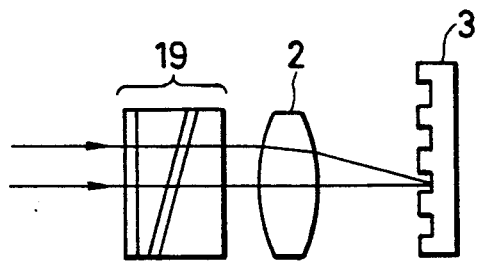
FIG. 14 is a view showing the seventh embodiment as being used.

FIGS. 13A and 13B show the seventh embodiment in which an optical low-pass filter 19 is arranged so that the separating angle θ of the light by the birefringence is continuously varied by continuously varying the voltage to be applied in the low-pass filter 16 of the above mentioned fifth embodiment (See FIGS. 9A and 9B). If this optical low-pass filter 19 is placed in front of the imaging lens 2, that is, in the part in which the incident rays are substantially parallel as shown in FIG. 14, its effect will be substantially the same as of the second embodiment (See FIGS. 4A and 4B) and the generation of the aberration will be little.

Figure 15:
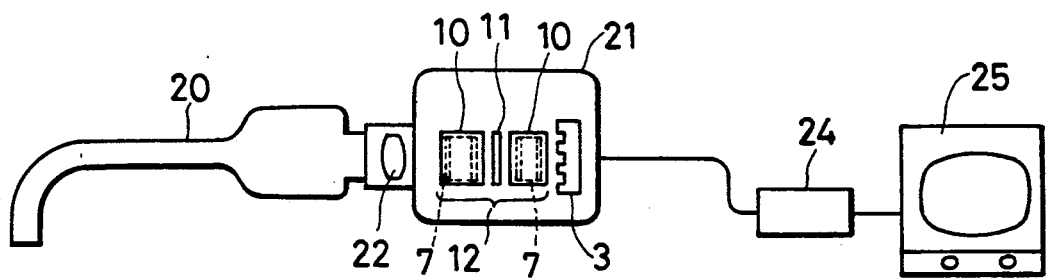
FIG. 15 is a view showing an example of using the low-pass filter of FIG. 6.
Figure 16:
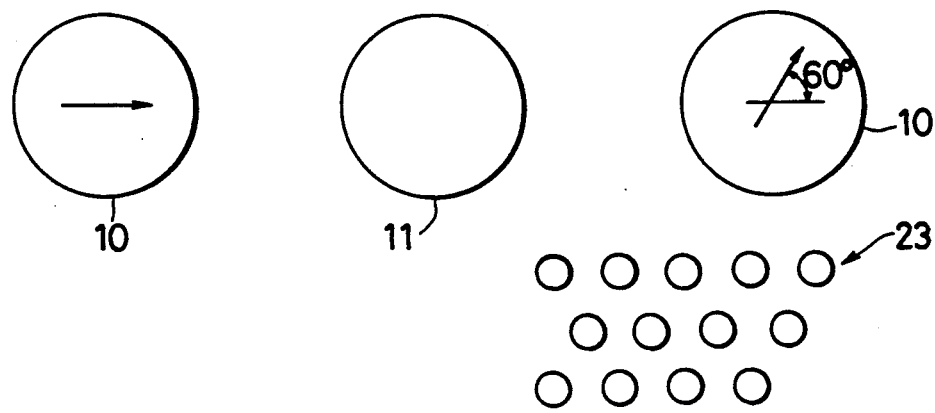
FIG. 16 is a view showing the structure of the low-pass filter in the using example of FIG. 15.
Figure 17A:
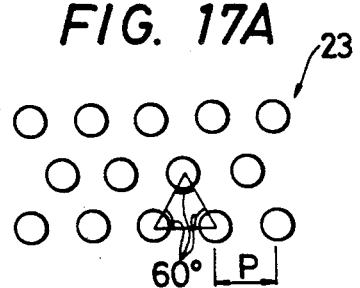
FIGS. 17A to 17D are views showing the relations between the distance of the respective fibers and the displacement of the image in the using example in FIG. 15.
Figures 17B, 17C, 17D:
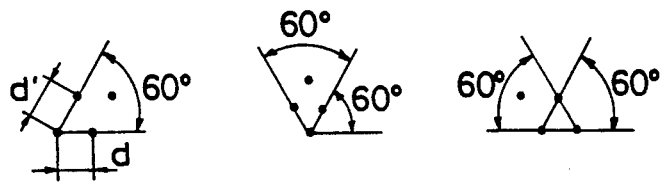

FIG. 15 shows an example of using the optical low-pass filter 12 shown in FIG. 6. In this example, in order to prevent the Moiré from being generated in case a television camera 21 is fitted to a fiberscope 20, the optical low-pass filter 12 is arranged between an adapter lens 22 and the CCD3. If the two low-pass filters 10, 10 forming this low-pass filter assembly 12 are arranged against the image 23 on the end face of the image guide of the fiberscope 20 so that the direction of each ray component separated is overlapped on each other at an angle of about 60 degrees by the ¼-wave plate 11 as shown in FIG. 16, the displacement of the image by the birefringence will be as shown in FIG. 17B. Symbols d and d' represent displaced distances of the image. Therefore, if the distance between the respective fibers is P and $$d \approx d' \approx \frac{P}{2} \tag{2}$$

the black parts (clad parts) in the image 23 will be filled by the birefringence and the Moiré will become minimum.

Now, in most cases, several kinds of the fiberscope 20 in which the distance P between the adjacent fibers in the image 23 of the end face of the image guide is different are attached to the television camera 21. Therefore, by selecting the one nearer to P/2 of $\Delta_1$ and $\Delta_2$ by switching on-off the voltage applied to the low-pass filter 10, the formula (2) can be substantially satisfied and the Moiré can be made minimum.

Or else, in case the distances between the adjacent fibers in two kinds of the fiberscope 20 to be attached to the television camera 21 are represented by P' and P'' (P' > P''), respectively, $$\left.\begin{array}{l} \Delta_1 \approx \frac{P}{2} \\ \Delta_2 \approx \frac{P'}{2} \end{array}\right\} \tag{3}$$

may be made. For that purpose, by using the formula (1), $\Delta_A$ and $\Delta_B$ may be selected so that $$\left.\begin{array}{l} \Delta_A + \Delta_B \approx \frac{P}{2} \\ \Delta_A - \Delta_B \approx \frac{P'}{2} \end{array}\right\} \tag{4}$$

may be made. That is to say $$\left.\begin{array}{l} \Delta_A = \frac{P + P'}{4} \\ \Delta_B = \frac{P - P'}{4} \end{array}\right\} \tag{5}$$

Figure 18:
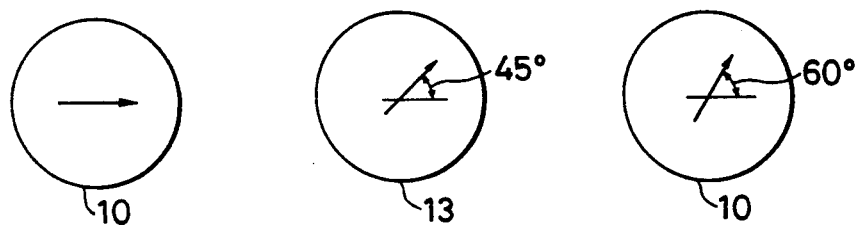
FIG. 18 is a view showing the other structures of the low-pass filter in the using example of FIG. 15.

By the way, the displaced direction of the light by the low-pass filter 10 may be as shown in FIGS. 17C and D. Also, instead of the ¼-wave plate 11, there may be used an optical rotatory plate rotating the plane of polarization by 45 degrees or a polarization canceling plate. Or else, as shown in FIG. 18, a thin birefringent plate 13 may be used. In this case, the displaced direction of the image by the birefringence may be 45 degrees or −45 degrees with respect to the displaced direction of the low-pass filter 10.

Also, as indicated by the dotted lines in FIG. 15, the low-pass filters 7 shown in FIGS. 4A and 4B may be used in place of the low-pass filter 10. In such case, if the applied voltage is varied whenever the fiberscope is exchanged so that $$\Delta \approx \frac{P}{2},$$

the Moiré will be able to be made minimum.

By the way, in FIG. 15, the reference numeral 24 represents a camera controlling unit and 25 represents a monitoring television.

Figure 19:
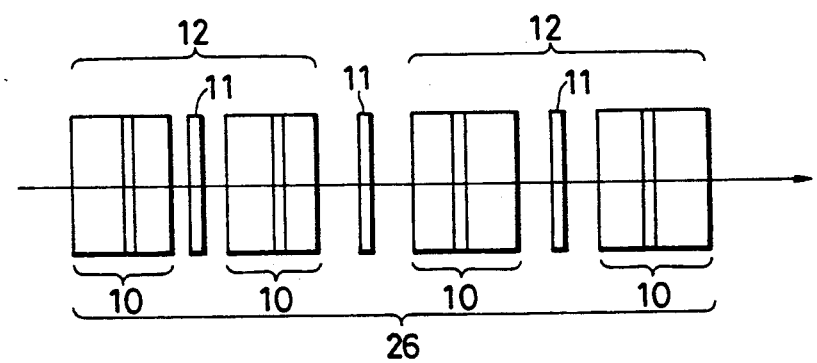
FIG. 19 is a schematic sectional view of the eighth embodiment.
Figure 20:
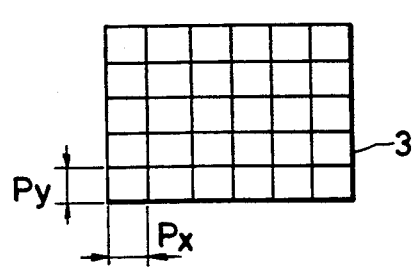
FIG. 20 is a view showing the size of a picture element of the CCD.

FIG. 19 shows the eighth embodiment in which an optical low-pass filter assembly 26 comprises two low-pass filters 12 and a ¼-wave plate 11 arranged between the two low-pass filters 12 in order to use in the case of combining the television camera 21 with the fiberscope 20 of FIG. 15. In this embodiment, however, the angle between the two ray components separated by the low-pass filter elements 10, 10 forming the low-pass filter 12 on the fiberscope 20 side is 60 degrees and the angle between the two ray components separated by the low-pass filter elements 10, 10 forming the low-pass filter 12 on the CCD3 side is 90 degrees. In this case, as shown in FIG. 20, if the lengths in the vertical direction and horizontal direction of a period of the Nyquist limit of one picture element of CCD3 or a mosaic filter are represented respectively by Px and Py, in order to cancel the Moiré and to elevate the resolving power of the television picture image of the fiberscope 20 having a distance P between two adjacent fibers, in case $$\left.\begin{array}{l} P > 2P_x \\ P_x \sin 60° > 2P_y \end{array}\right\} \tag{7}$$

there may be made $$\left.\begin{array}{l} d \approx d' \approx \Delta_2 \approx 0 \\ \Delta_4 \approx \frac{P_x}{2} \\ \Delta_6 \approx \frac{P_y}{2} \end{array}\right\} \tag{8}$$

Further, if $$\left.\begin{array}{l} P < 2P_x \\ P_x \sin 60° < 2P_y \end{array}\right\} \tag{9}$$

there may be made $$\left.\begin{array}{l} d \approx d' \approx \Delta_1 \approx \frac{P}{2} \\ \Delta_3 \approx \Delta_5 \approx 0 \end{array}\right\} \tag{10}$$

wherein $\Delta_4$, $\Delta_6$, $\Delta_3$ and $\Delta_5$ represent the displacement of the image shown respectively in FIGS. 7A to 7D.

The significance of these formulae (7) to (10) is that, if the image of the end face of the image guide and the finer one of the periodic structure corresponding to the Nyquist frequency of the picture element of the CCD3 or the mosaic filter are canceled by the birefringence, the reduction of the resolving power will be little and the Moiré will be removed. Therefore, the voltage to be applied to the low pass filter 26 may be varied to satisfy the formulae (7) to (10).

Figure 21:
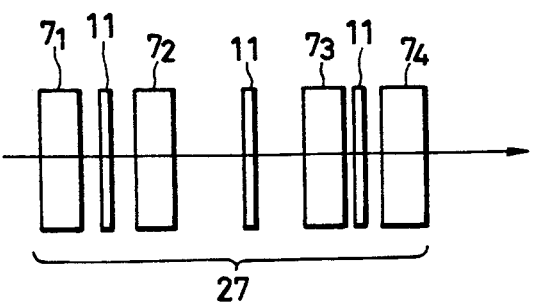
FIG. 21 is a schematic sectional view of the ninth embodiment.
Figure 22A:
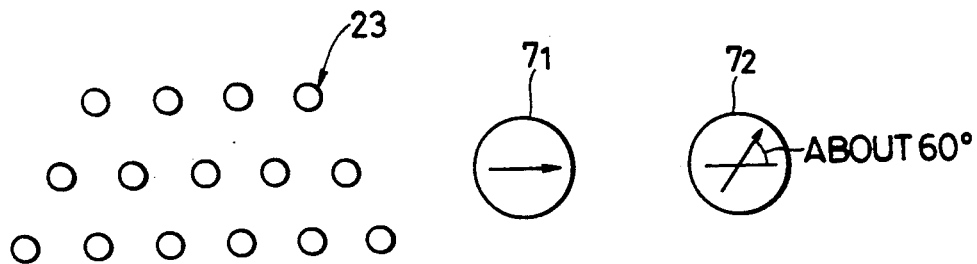
FIGS. 22A and 22B are views showing the directions of the birefringence of the ninth embodiment.
Figure 22B:
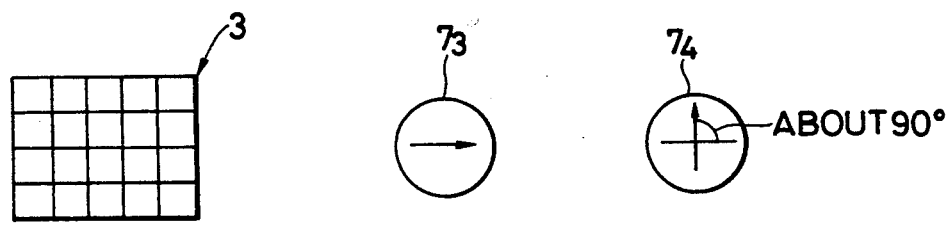

FIG. 21 shows the ninth embodiment which is different from the eighth embodiment in respect that a low-pass filter assembly 27 is formed by using the low-pass filters $7_1$, $7_2$, $7_3$ and $7_4$ of the same structure as of the low-pass filter 7 shown in FIGS. 4A and 4B instead of the low-pass filter elements 10, 10 in the eighth embodiment shown in FIG. 19. The birefringent directions of the low-pass filters $7_1$, $7_2$, $7_3$ and $7_4$ are as shown in FIGS. 22A and 22B.

By the way, in the above mentioned eighth and ninth embodiments, anything converting the linearly polarized light to a circularly polarized light or naturally polarized light such as a polarization canceling plate may be used instead of the ¼-wave plate 11. Also, the arrangement of the two low-pass filter assemblies 12, 12 may be reversed and, in such case, the birefringent plate 13 of a birefringent direction of 45 degrees may used instead of the ¼-wave plate 11.

Figure 23A:
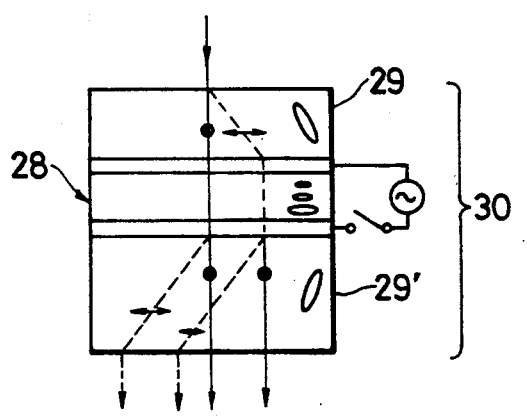
FIGS. 23A and 23B are schematic sectional views of the tenth embodiment.
Figure 23B:
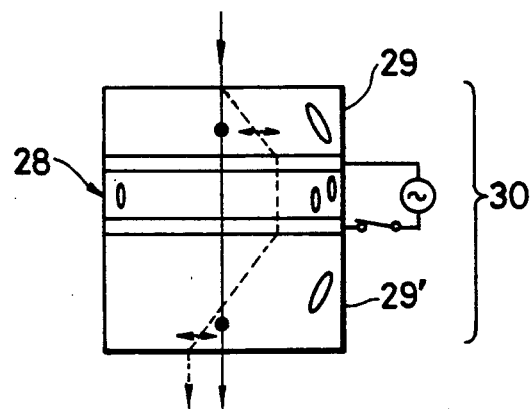
Figure 24:
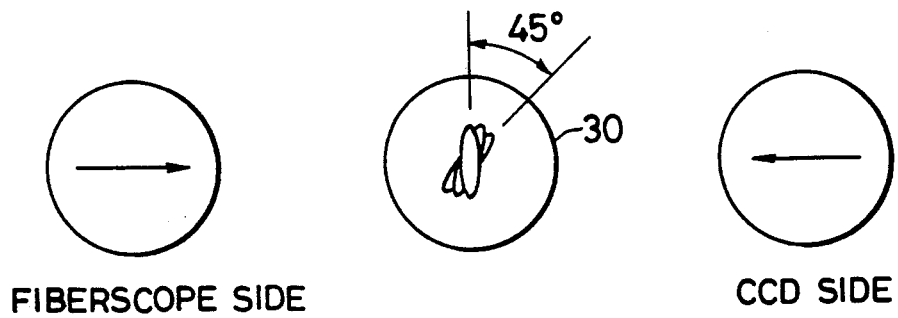
FIG. 24 is a view of the tenth embodiment as seen from the incident direction of rays of light.

FIGS. 23A and 23B show the tenth embodiment in which a low-pass filter 30 comprises a 45-degree twisted nematic type liquid crystal device 28 and two crystal plates 29, 29' arranged so that the inclinations of the crystal axes may be reverse to each other in front and rear of the liquid crystal device 28. This low-pass filter 30 is formed so that the separation amount of the ray components in the crystal plates 29, 29' is varied by varying the inclinations of the crystal axes, thicknesses, qualities of the material or the like of the crystal plates 29, 29'. When no voltage is applied between the transparent electrodes (FIGS. 23A), the light will be separated into four rays since the liquid crystal element 28 acts in the same manner as the 45-degree optical rotatory plate but, when a voltage is applied between the electrodes (FIGS. 23B), the orientation of the liquid crystal will become vertical and therefore the light will be separated into two ray components. Thereby, the characteristics as of an optical low-pass filter will vary. FIG. 24 shows the low-pass filter 30 as seen in the incident direction of the light. The arrows indicate the directions of separating the light by the birefringence of the crystal plates 29 and 29'.

By the way, the liquid crystal device has been used in each of the above mentioned embodiments but, as described below, such electrooptic device as a PLZT or DKDP may be used in place of the liquid crystal. The PLZT is an electrooptic ceramic polycrystal made by adding several mol % $La_2O_3$ to a solid solution $Pb(Zr, Ti)O_3$ of $PbTiO_3$ and $PbZrO_3$ and represented by the chemical formula $(Pb_{1-x}, La_x)$ $(Zr_y, Ti_{1-y})_{1-x/4}O_3$. DKDP is represented by the chemical formula $KD_2PO_4$.

Figure 25:
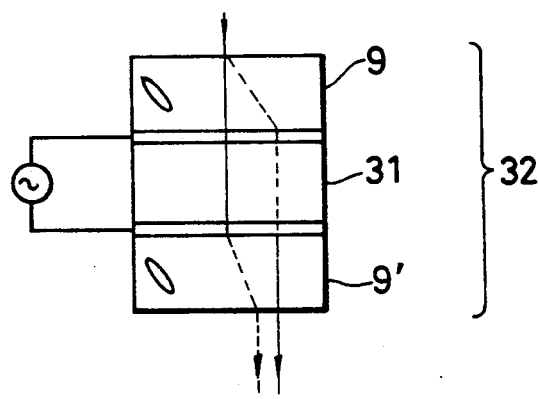
FIG. 25 is a schematic sectional view of the eleventh embodiment.

FIG. 25 shows the eleventh embodiment in which a low-pass filter 32 is formed by arranging the crystal plates 9 and 9' in front and rear of a PLZT 31 and developing the same function as of the third embodiment shown in FIGS. 5A and 5B with the variation of the applied voltage.

Figure 26:
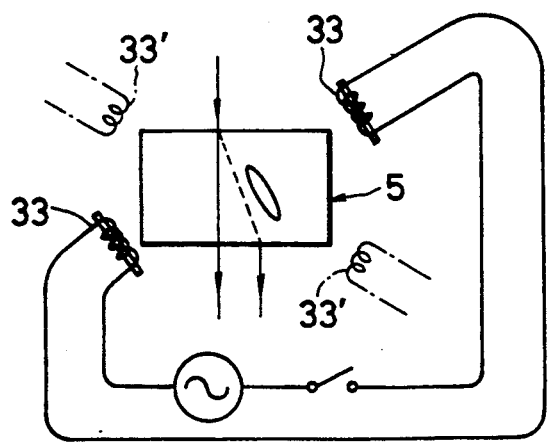
FIG. 26 is a view showing a structure of varying the orientation and refractive index with the variation of the magnetic field.

The orientation of the liquid crystal device or electrooptic device is varied with the switching on-off of the applied voltage or the variation of the size of the applied voltage in each of the above mentioned embodiments but the orientation and refractive index may be varied with the variation of the current source frequency or the variation of the magnetic field by electromagnets 33, 33 as shown in FIG. 26. Also, the characteristics as of an optical low-pass filter may be varied by varying the characteristics of the liquid crystal by applying heat, for example, with heaters 33', 33' as indicated by the chain lines in FIG. 26.

Figure 27A:
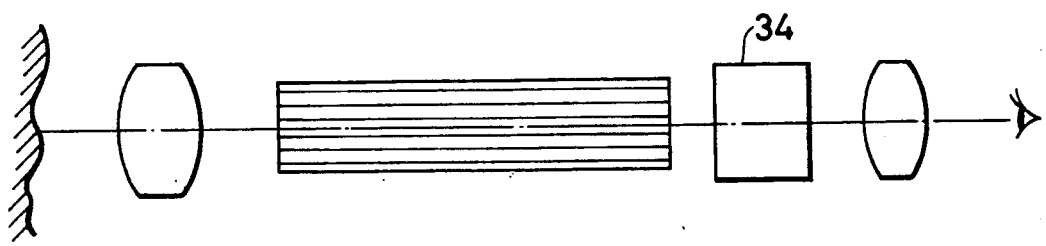
FIGS. 27A to 27D are views showing other using examples.
Figure 27B:
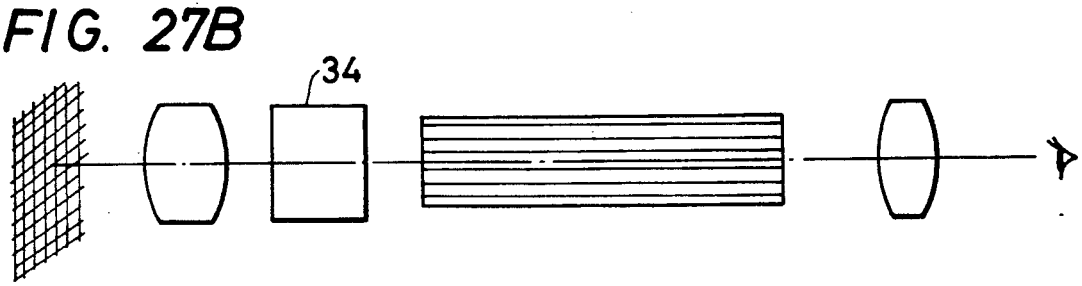
Figure 27C:
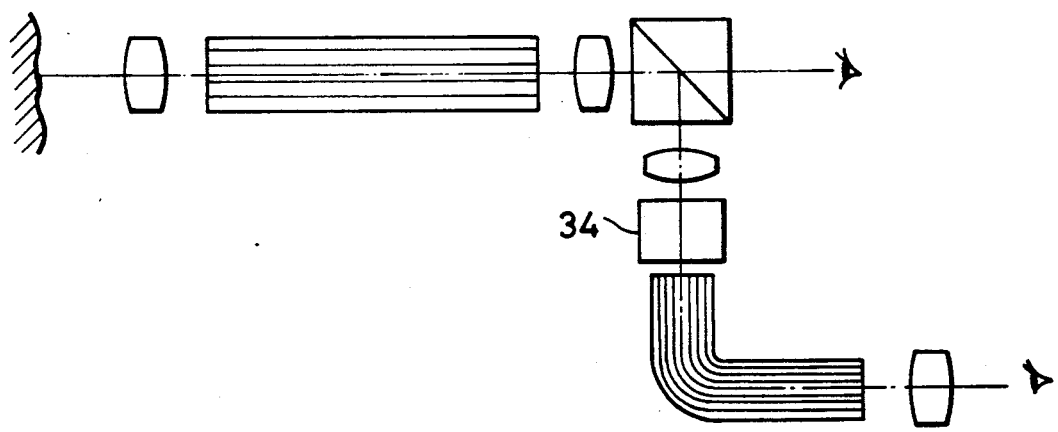
Figure 27D:
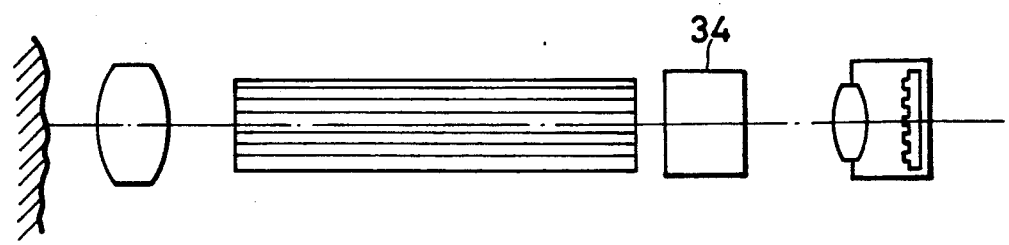

Also, the low-pass filter according to the present invention may be placed within the fiberscope as shown in FIGS. 27A to 27D. That is to say, FIG. 27A shows an example using a low-pass filter 34 to remove the mesh of the fiberscope, FIG. 27B shows an example using the low-pass filter 34 to remove the Moiré in the case of observing an object having a geometrical pattern-shaped device, FIG. 27C shows an example using the low-pass filter 34 to remove the Moiré generated in a lecturescope and FIG. 27D shows an example using the low-pass filter 34 to remove the Moiré in the case using a television camera instead of the eye in the example in FIG. 27A. By the way, it is needless to say to be possible to arrange such solid-state image sensor as a CCD in the position corresponding to the light entrance end face of the image guide fiber bundle instead of said fiber bundle in FIGS. 27B and 27C. Further, the optical low-pass filter according to the present invention can be also utilized to TV cameras equipped with an imaging device comprising a color encoding stripe filter and pickup tube combined with each other instead of the solid-state image sensor.

Also, the low-pass filter according to the present invention may be placed within an adapter lens of a TV camera, within the TV camera body or simultaneously within two or more of the above. Further, the low-pass filter according to the present invention may be divided and may be arranged as dispersed within a fiberscope, adapter lens of a TV camera and TV camera body.

As described above, the low-pass filter according to the present invention has such practically important advantages that, in case it is used for a television camera, electronic camera or fiberscope, the Moiré will be able to be removed and the thickness will be able to be made smaller without so much reducing the resolving power.

What is claimed is:

1. An image pick-up system comprising a television camera having built-in image pick-up means, an adapter lens contributing to image formation of an object to be photographed on said image pick-up means, and the optical low-pass filter being arranged between said adapter lens and said image pick up means, said optical low-pass filter comprises a first low-pass filter member comprising a first twisted nematic type liquid crystal device arranged to vary its optical rotatory power and a pair of first birefringent plates respectively arranged in front and rear of said liquid crystal device and having crystal axes inclined in the same direction with respect to the incident optical axis; a second low-pass filter member comprising a second twisted nematic type liquid crystal device aligned in a direction in which light travels with respect to said first low-pass filter member and arranged to vary its optical rotatory power and a pair of second birefringent plates respectively arranged in front and rear of said second liquid crystal device and formed so that the plane including the respective crystal axes directed in the same direction intersects the plane including the crystal axes of said first birefringent plates; and any one of a ¼-wave plate, polarization canceling plate, ±45-degree optical rotatory plate and birefringent plate interposed between said first low-pass filter member and said second low-pass filter member.

2. An optical low-pass filter comprising an N-type liquid crystal device provided with a front surface vertical to an incident optical axis and a back surface inclined to the incident optical axis, having birefringent characteristics and being able to separate spatially incident light into an ordinary ray component and extraordinary ray component, and a prism free of birefringent characteristics in which one surface is parallel with one of said front surface and said back surface of said liquid crystal device and the other surface is perpendicular to the incident optical axis.

3. An image pick-up system comprising an imaging lens, image pick-up means receiving an object image formed by said imaging lens, and an optical low-pass filter arranged between a plane of incidence of said imaging lens and said image pick-up means, wherein:

said optical low-pass filter comprises an N-type liquid crystal device provided with a front surface vertical to an incident optical axis and a back surface inclined to the incident optical axis, having birefringent characteristics and being able to separate spatially incident light into an ordinary ray component and extraordinary ray component; and a prism free of birefringent characteristics in which one surface is parallel with one of said front surface and said back surface of said liquid crystal device and the other surface is perpendicular to the incident optical axis.

4. An image pick-up system comprising an imaging lens, image pick-up means receiving an object image formed by said imaging lens, and are optical low-pass filter arranged in front of said imaging lens, wherein:

said optical low-pass filter comprises an N-type liquid crystal device provided with a front surface vertical to an incident optical axis and a back surface inclined to the incident optical axis and, having birefringent characteristics and being able to separate spatially incident light into an ordinary ray component and extraordinary ray component; and a prism free of birefringent characteristics in which one surface is parallel with one of said front surface and said back surface of said liquid crystal device and the other surface is perpendicular to the incident optical axis.

5. An image pick-up system comprising a television camera having built-in image pick-up means, an adapter lens contributing to image formation of an object to be photographed on said image pick-up means, and an optical low-pass filter arranged between said adapter lens and said image pick-up means, wherein:

said optical low-pas filter comprises liquid crystal means having birefringent characteristics and being able to separate spatially an incident light into an ordinary ray component and extraordinary ray component, said liquid crystal means being without polarizers on the incident and exit sides thereof, and said liquid crystal means comprises a first liquid crystal device arranged so as to be able to vary the direction of the crystal axis with respect to the incident optical axis; a second liquid crystal device aligned adjacently with said first liquid crystal device and arranged so as to be able to vary the direction of the crystal axis with respect to the incident optical axis; and any one of a ½-wave plate, optical rotary plate and twisted nematic type liquid crystal device interposed between said first liquid crystal device and said second liquid crystal device.

6. An optical low-ass filter comprising a first liquid crystal device, without polarizers on the incident and exit sides thereof, wherein:

said first liquid crystal device being so arranged that the direction of the crystal axis of said first liquid crystal device may be inclined with respect to the incident optical axis when light enters said first liquid crystal device, and the incident light entering said first liquid crystal device is separated spatially into an ordinary ray component and extraordinary ray component by birefringent characteristics of said first liquid crystal device and said two separated ray components being emitted from said first liquid crystal device.

7. An optical low-pass filter according to claim 6 wherein an angle between said direction of the crystal axis of the first liquid crystal device and said incident optical axis is variable.

8. An optical low-pass filter comprising a twisted nematic type liquid crystal device without polarization plates on the incident and exit sides thereof, wherein:

said twisted nematic type liquid crystal device is so arranged that an optical rotatory power of the liquid crystal device can be varied, a first birefringent plate is arranged on an incident side of said liquid crystal device and a second birefringent plate being arranged on an emitting side of said liquid crystal device, and incident light is spatially separated into an ordinary ray component and extraordinary ray component by said first birefringent plate and said two separated ray components are emitted form said first birefringent plate to be incident on said twisted nematic type liquid crystal device.

9. An optical low-pass filter according to claim 8, wherein:

the directions of the crystal axes of said first and second birefringent plates are substantially the same, and said directions of the crystal axes are inclined with respect to an incident optical axis when light enters said liquid crystal device.

10. An optical low-pass filter according to claim 8 wherein the directions of the crystal axes of said first and second birefringent plates are reverse to each other with respect to the incident optical axis.

11. An optical low-pass filter according to claim 9 wherein said liquid crystal device is able to have a first condition in which said ordinary ray components and extraordinary ray components emitted from said first birefringent plate are received by said liquid crystal device itself and are emitted from said liquid crystal device itself without changing the directions of respective polarization planes of the ordinary ray components and extraordinary ray components and to have a second condition in which said ordinary ray components and extraordinary ray components emitted from said first birefringent plate are received by said liquid crystal device itself and are emitted from said liquid crystal device itself in a state that the directions of respective polarization planes of the ordinary ray components and extraordinary ray components are rotated at an angle of 45 degrees with respect to the original directions of respective polarization planes of the two ray components.

12. An optical low-pass filter according to claim 8, wherein:

any one of an optical device which changes the properties of polarization, an optical device which cancels polarization, an optical device which changes the direction of polarization and a birefringent plate is arranged on an emitting side of said twisted nematic type liquid crystal device, a second optical low-pass filter member is arranged on the emitting side of any one of said optical device and birefringent plate, said second optical low-pass filter member comprises a second twisted nematic type liquid crystal device, said second twisted nematic type liquid crystal device is so arranged that an optical rotatory power of the liquid crystal device can be varied, and a third birefringent plate is arranged on an incident side of said second twisted nematic type liquid crystal device and a fourth birefringent plate is arranged on an emitting side of said second twisted nematic type liquid crystal device.

13. An optical low-pass filter according to claim 12, wherein:

the directions of the crystal axes of said first and second birefringent plates are substantially the same, the directions of the crystal axes of said third and fourth birefringent plates are substantially the same, said first, second, third and fourth birefringent plates are so arranged that the plane including the crystal axes of the first and second birefringent plates may intersect the plane including the crystal axes of the third and fourth birefringent plates.

14. An optical low-pass filter according to claim 12 wherein said optical device which changes the properties of polarization is a ½-wave plate.

15. An optical low-pass filter according to claim 13 wherein said optical device which changes the properties of polarization is a ½-wave plate.

16. An optical low-pass filter according to claim 7, further comprising;

any one of an optical device for changing the properties of polarization, an optical device for cancelling polarization, an optical device for changing the direction of polarization and a birefringent plate, which is arranged on an emitting side of said first liquid crystal device, and a second liquid crystal device arranged on an emitting side of said optical device, said second liquid crystal device being so arranged that the direction of the crystal axis of the second liquid crystal device is inclined with respect to the incident optical axis when light enters said second liquid crystal device, an angle between said direction of the crystal axis of the second liquid crystal device and said incident optical axis being variable.

17. An optical low-pass filter according to claim 16 where said optical device having the properties which change the direction of the polarization plane is any one of a ½-wave plate, optical rotatory plate and twisted nematic type liquid crystal device.

18. An optical low-pass filter according to claim 16 wherein an angle between said crystal axis of said first liquid crystal device and said incident optical axis and angle between said crystal axis of said second liquid crystal device and said incident optical axis synchronously vary with respect to each other.

19. An optical low-pass filter according to claim 16 wherein an angle between the crystal axis of said first liquid device and the incident optical axis and an angle between the crystal axis of said second liquid crystal device and the incident optical axis continuously and periodically vary.

20. An optical low-pass filter according to claim 13 wherein said plane including the crystal axes of the first and second birefringent plates substantially intersects at an angle of 60 degrees with said plane including the crystal axes of the third and fourth birefringent plates.

21. An optical low-pass filter according to claim 20, wherein:

any one of an optical device which changes the properties of polarization, an optical device which changes the direction of polarization, an optical device which cancels polarization and a birefringent plate is arranged on an emitting side of said fourth birefringent plate, a third optical low-pass filter member is arranged on an emitting side of said optical device and birefringent plate, said third optical low-pass filter member comprises a third twisted nematic type liquid crystal device, said third twisted nematic type liquid crystal device is so arranged that an optical rotatory power of the liquid crystal device can be varied, a fifth birefringent plate is arranged on an incident side of said third twisted nematic type liquid crystal device and a sixth birefringent plate is arranged on an emitting side of said third twisted nematic type liquid crystal device, any one of an optical device which changes the properties of polarization, an optical device which cancels polarization, an optical device which change the direction of polarization and a birefringent plate is arranged on an emitting side of said sixth birefringent plate, a fourth optical low-pass filter member is arranged on an emitting side of any one of said optical devices and birefringent plate, said fourth optical low-pass filter member comprises a fourth twisted nematic type liquid crystal device, said fourth twisted nematic type liquid crystal device is so arranged that an optical rotatory power of the liquid crystal device can be varied, a seventh birefringent plate is arranged on an incident side of said fourth twisted nematic type liquid crystal device and an eight birefringent plate is arranged on an emitting side of said fourth twisted nematic type liquid crystal device, the directions of the crystal axes of said fifth and sixth birefringent plates are substantially the same, the directions of the crystal axes of said seventh and eighth birefringent plates are substantially the same, said fifth, sixth, seventh and eighth birefringent plates are so arranged that the plane including the crystal axes of the fifth and sixth birefringent plates may intersect the plane including the crystal axes of the seventh and eighth birefringent plates, and said plane including the crystal axes of the fifth and sixth birefringent plates intersects at an angle of 90 degrees with said plane including the crystal axes of the seventh and eighth birefringent plates.

22. An optical low-pass filter according to claim 16, wherein:
- an optical device having the properties which change the direction of the polarization plane is arranged on an emitting side of said second liquid crystal device,
- a second optical low-pass filter member is arranged on an emitting side of said optical device,
- said second optical low-pass filter member comprises a third liquid crystal device,
- said third liquid crystal device is so arranged that the direction of the crystal axis of said third liquid crystal device may be inclined with respect to the incident optical axis when light enters said third liquid crystal device,
- the incident light entering said third liquid crystal device is separated into an ordinary ray component and extraordinary ray component by birefringent characteristics of said third liquid crystal device and said two separated ray components are emitted from said third liquid crystal device,
- an angle between said direction of the crystal axis of the third liquid crystal device and said incident optical axis is variable,
- said second optical low-pass filter member further comprises an optical device which is arranged on an emitting side of said third liquid crystal device and has the properties changing the direction of the polarization plane and a fourth liquid crystal device arranged on an emitting side of said optical device,
- said fourth liquid crystal device is so arranged that the direction of the crystal axis of the fourth liquid crystal device may be inclined with respect to an incident optical axis when light enters said fourth liquid crystal device,
- an angle between said direction of the crystal axis of the fourth liquid crystal device and said incident optical axis is variable.

23. An optical low-pass filter according to claim 10 wherein said liquid crystal device is able to have a first condition in which said ordinary ray component and extraordinary ray components emitted from said first birefringent plate are received by said liquid crystal device itself and are emitted from said liquid crystal device itself without changing the directions of respective polarization planes of the ordinary ray components and ordinary ray components and to have a second condition in which said ordinary ray components and extraordinary ray components emitted from said first birefringent plate are received by said liquid crystal device itself and are emitted from said liquid crystal device itself in a state that the directions of respective polarization planes of the ordinary way components and extraordinary ray components are rotated at an angle of 45 degrees with respect to the original directions of respective polarization planes of the two ray components.

24. An image pick-up system for endoscopes comprising an endoscope having an image guide fiber bundle and the optical low-pass filter arranged on the side of an exit end face of the image guide fiber bundle of said endoscope, wherein:
- said optical low-pass filter includes any one of an optical low-pass filter comprising liquid crystal device having birefringent characteristics and being able to separate spatially an incident light into an ordinary ray component and extraordinary ray component and optical low-pass filters according to one of claims 6 through 22 or 23.

25. An image pick-up system for endoscopes comprising an endoscope having an image guide fiber bundle and the optical low-pass filter arranged on the side of an exit end face of the image guide fiber bundle of said endoscope, wherein:
- said optical low-pass filter includes any one of an optical low-pass filter comprising electrooptic means having birefringent characteristics and being able to separate an incident light into an ordinary ray component and extraordinary ray component and optical low-pass filters according to one of claims 6 through 22 or 23.

26. An image pick-up system for endoscopes comprising:
- a fiberscope;
- an imaging lens system to form an image of an exit end face of an image guide fiber bundle of said fiberscope;
- image pick-up means to photograph the image formed by said imaging lens system; and
- an optical low-pass filter according to one of claims 6 through 22 or 23, which is arranged between the exit end face of the image guide fiber bundle of said fiberscope and said image pick-up means.

27. An observing system for endoscopes comprising:
- a fiberscope having an image guide fiber bundle;
- a lecturescope having an image guide fiber bundle;
- an optical system in which an image of the exit end face of the image guide fiber bundle of said fiberscope is formed on the entrance end face of the image guide fiber bundle of said lecturescope; and
- any one of optical low-pass filters according to one of claims 6 through 22 or 23, an optical low-pass filter comprising a liquid crystal device having birefringent characteristics and being able to separate spatially an incident light into an ordinary ray component and extraordinary ray component and an optical low-pass filter comprising electrooptic means having birefringent characteristics and being able to separate spatially an incident light into an ordinary ray components and extraordinary ray components being arranged between said exit end face of the image guide fiber bundle of the fiberscope and said entrance end face of the image guide fiber bundle of the lecturescope.

28. An image pick-up system for endoscopes comprising:
- a fiberscope;
- an imaging lens system to form an image of an exit end face of an angle guide fiber bundle of said fiberscope;
- image pick-up means to photograph the image formed by said imaging lens system; and
- one of an optical low-pass filter comprising a liquid crystal device having birefringent characteristics and being able to separate spatially an incident light into an ordinary ray components and extraordinary ray components and an optical low-pass filter comprising electrooptic mans having birefringent characteristics and being able to separate spatially an incident light into an ordinary ray components and extraordinary ray components which is arranged between the exit end face of the image guide fiber bundle of said fiberscope and said image pick-up means.

29. An optical low-pass filter comprising an electrooptic ceramic polycrystal element; without polarizers on the incident and exist sides thereof,
   said electrooptic ceramic polycrystal element being provided with a pair of birefringent plates disposed in front and rear thereof and being arranged so that its optical rotatory power is varied,
   said pair of birefringent plates having crystal axes inclined with respect to an incident optical axis.

* * * * *